United States Patent
Pastyr et al.

(10) Patent No.: US 7,132,674 B2
(45) Date of Patent: Nov. 7, 2006

(54) COLLIMATOR FOR HIGH-ENERGY RADIATION AND PROGRAM FOR CONTROLLING SAID COLLIMATOR

(75) Inventors: Otto Pastyr, St. Ilgen (DE); Gernot Echner, Wiesenbach (DE); Wolfgang Schlegel, Heidelberg (DE); Günther Hartmann, Heidelberg (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 102 days.

(21) Appl. No.: 10/495,967

(22) PCT Filed: Oct. 23, 2002

(86) PCT No.: PCT/EP02/11812

§ 371 (c)(1),
(2), (4) Date: Feb. 3, 2005

(87) PCT Pub. No.: WO03/043698

PCT Pub. Date: May 30, 2003

(65) Prior Publication Data

US 2005/0141671 A1 Jun. 30, 2005

(30) Foreign Application Priority Data

Nov. 23, 2001 (DE) ............................... 101 57 523

(51) Int. Cl.
*G21K 1/02* (2006.01)
*A61N 5/00* (2006.01)

(52) U.S. Cl. .................. 250/505; 250/492.1; 378/65; 378/147; 378/148; 378/150

(58) Field of Classification Search .................. None
See application file for complete search history.

(56) References Cited

U.S. PATENT DOCUMENTS 4,359,642 A 11/1982 Heinz (Continued)

FOREIGN PATENT DOCUMENTS

DE 694 06 898 3/1998

(Continued)

*Primary Examiner*—Jack I. Berman
(74) *Attorney, Agent, or Firm*—Paul Vincent

(57) ABSTRACT

The invention relates to a collimator (1) for defining a beam of energetic rays (2) which is emitted from an essentially punctiform radiation source (3) and is oriented onto an object (1) to be treated. The collimator is especially used for the stereotactic conformation radiotherapy of tumors. The collimator (1) is embodied in such a way that an irregular object (4) can be scanned by rays (2, 2') which are defined by an opening in the collimator. The invention also relates to a program for controlling the collimator. In order to define the contours (29, 29', 29") of the objects (4) to be irradiated in a simple but highly accurate manner, especially with a precise definition of the irradiation fields, the collimator comprises a plurality of different sized openings (5, 5' 5"). One of the openings (5, 5', 5") can be selectively displaced in a polydirectional manner on a strip (6) having a spherical surface, and the central axis (7) thereof is oriented towards the radiation source (3). The other collimator openings (5', 5") are shielded form the rays (2). A control system (9) acts on the drives (23, 24, 25) of a drive device (8) in such a way that large openings (5, 5') are used to scan large irradiation surfaces (26) of the object to be treated (4), and small openings (5', 5") are used for precise definition at the edge of the irradiation surfaces (26) of the object to be treated (4), especially in the event of irregular contours (29, 29', 29").

38 Claims, 6 Drawing Sheets

U.S. PATENT DOCUMENTS

| | | | |
|---|---|---|---|
| 4,489,426 A * | 12/1984 | Grass et al. | 378/150 |
| 5,278,886 A | 1/1994 | Kobiki | |
| 5,332,908 A | 7/1994 | Weidlich | |
| 6,389,108 B1 * | 5/2002 | Ein-Gal | 378/147 |
| 2001/0043669 A1 | 11/2001 | Ein-Gal | |
| 2004/0184579 A1 * | 9/2004 | Mihara et al. | 378/65 |

FOREIGN PATENT DOCUMENTS

| | | |
|---|---|---|
| DE | 196 04 789 | 8/1999 |
| DE | 199 05 823 | 6/2000 |
| DE | 199 36 068 | 2/2001 |
| DE | 199 50 794 | 6/2001 |
| EP | 0 382 560 | 8/1990 |

* cited by examiner

COLLIMATOR FOR HIGH-ENERGY RADIATION AND PROGRAM FOR CONTROLLING SAID COLLIMATOR

This application is the national stage of PCT/EP02/11812 filed on Oct. 23, 2002 and claims Paris Convention priority of DE 101 57 523.8 filed Nov. 23, 2001

BACKGROUND OF THE INVENTION

The invention concerns a collimator for defining a beam of high energy radiation which is emitted from a substantially punctiform radiation source and directed onto an object to be treated for, in particular, stereotactic conformation radiation of tumors, wherein the collimator is designed to scan an irregular object to be treated with beams which are defined by a collimator opening.

Collimators are used for conform and high-dosed radiation of target volumes having complicated shapes. There are various conventional types of collimators which usually require large amounts of time and/or great technical effort to obtain high accuracy, in particular exact definition of the radiation fields.

Compensators are particularly time-consuming, since a shaped collimator must be produced for each surface to be irradiated, and the shaped collimators on the radiation devices must be changed when changing the individual irradiation directions.

To reduce this time, multi-leaf collimators are normally used. DE 199 05 823 C1 discloses an example of such a collimator. The shaping is thereby obtained using a plurality of collimator sheets (leafs), with each leaf having a motor, a path detector, and a control for the orientation of the front edge of the leaf in accordance with the path of the rays. This effort is required for a total of between 80 and 120 leaves, wherein the leaves must be adjusted for each surface to be irradiated and for generating different radiation intensities.

SUMMARY OF THE INVENTION

A collimator of the above-mentioned type is disclosed in DE 199 22 656 A1. In this device, an electron beam is deflected by a magnetic field and thereby scanned, wherein the scanned beam is thereafter converted into a photon beam for irradiation. The collimator is thereby a further development of this object to obtain an even more exact point of radiation. If the collimator is formed as simple opening, the overall structure of the device is still complicated, in particular in the embodiment variant of FIG. 3, wherein the collimator opening must be moved synchronously with the scanned beam.

This collimator is particularly disadvantageous in that the accuracy for defining the edges of the radiation fields depends on the size of the spot to be irradiated, which is formed by means of the collimator opening determined for this collimator. Large radiation spots associated with large collimator openings increase the scanning speed but produce more inaccuracies. Vice versa, small radiation spots result in slow scanning but lead to a more exact reproduction of the radiation field borders.

It is therefore the underlying purpose of the invention to generate the contours of the objects to be treated with less expense but with more accuracy and in particular with an exact definition of the radiation fields.

One additional object is to vary the intensity of radiation for different partial regions of the objects to be treated in a fast and simple manner.

This object is achieved in accordance with the invention in that several collimator openings of different sizes are provided, wherein a selected one of the openings is displaceable in any direction along a spherical surface-shaped path, the central axis thereof being oriented towards the radiation source, and wherein the other collimator openings are shielded from radiation, and a control unit is designed to act on the drives of a drive means such that, for scanning large radiation surfaces of the object to be treated, large collimator openings are used, and for exact delimitation at the edge of the radiation surfaces of the object to be treated, in particular in case of irregular contours, small collimator openings are used.

With regard to the program, this object is achieved in that it controls the drive means via a computer such that an object to be treated can be irradiated in accordance with the predetermined contours, wherein it selects the size of the collimator opening which is optimum for forming the contour through actuating the further drive, and mutually matches the scanning processes carried out with the various collimator openings to obtain the required irradiation.

The inventive subject matter substantially simplifies the scanning process, since the definition lines can be scanned with high accuracy through radiation with a very small collimator opening thereby leaving a residual surface which can be scanned with a medium or larger collimator opening in a substantially shorter time.

To achieve the additional object, the inventive subject matter also permits control such that the dwell time of the beams, in particular the scanning speed, can be controlled by the above-mentioned drive means. The additional object is achieved, in particular, by a program which permits a computer loaded with this program to control the dwell time, in particular the scanning speed, through the above-mentioned drive means to obtain different radiation intensities.

The proposed technical solution requires substantially less effort than the above-mentioned multi-leaf collimators, since contours of radiation fields can be generated by a drive means which is formed from two, or maximally three individual drives. Path detection is also facilitated. Setting of the front edge of the leaves is also not required. In dependence on the size of the collimator opening, a radiation surface of any small or large size can be generated and guided over surfaces of any complicated shapes in accordance with the scanning scheme. It is also thereby possible to select non-irradiated areas within an overall surface to be irradiated. This is not possible with collimators defining the complete surface. The same also applies for surfaces of different radiation intensities with arbitrary arrangement. This permits loading of an object to be treated with different radiation intensities with reference to the area without any limits with regard to the possible shapes.

The at least one collimator opening is preferably designed to have defining walls which extend in the direction of the path of rays, i.e. conically thereby providing exact definition of the field to be irradiated and preventing generation of any partial shadows. A partial shadow is generated when the limits of the conventional collimators contained regions in which the beams were partially shielded by the associated material thickness of the collimator. This problem occurs, in particular, with multi-leaf collimators, since adjustment of the leaves results in the beams extending at different angles for each leaf position. In the above-mentioned multi-leaf collimator, this problem was solved by providing the front edges with a certain angle of inclination in dependence on the leaf adjustment. This required complicated actuation on all existing leaves. The above-mentioned embodiment of the invention solves this problem in a very simple fashion, since the collimator opening scanning the radiation field moves on a spherical surface-shaped path and is always substantially oriented towards the essentially punctiform radiation source, such that the limits always extend in the direction of the path of rays, thereby preventing partial shadows. The at least one collimator opening may thereby have any shape: it may e.g. be round or rectangular. With regard to the selected shape, one must assure that the radiation time for each scanning point corresponds to the radiation time dictated by the treatment plan.

The collimator is preferably designed such that several, preferably three collimator openings are disposed to be rotatable about an imaginary circular path. This design is advantageous since it permits switching from one collimator opening to one of the two other opening sizes by rotation through 120° without having to skip an intermediate collimator opening. This permits switching over even during beam loading thereby preventing irradiation of the object to be treated with intensities which cannot be controlled. The circular path is then advantageously designed such that the collimator opening, which is located in the working position, is always oriented in accordance with the invention and the other collimator openings are shielded. The rotation through 120° causes a desired collimator opening to replace a previous opening without requiring alignment, since the centers of the collimator openings are all located on the imaginary circular path. Orientation of the central axis of a collimator opening towards the radiation source is also always ensured when it is in its working position.

In the above-mentioned embodiments, the collimator openings are preferably located on a cylindrical part of shielding material which can be rotated by a revolver-like mechanism and be at least fixed in the working positions. The cylindrical part may thereby be rotatably disposed in a shielding block.

The at least one collimator opening can preferably be replaced by at least one collimator opening having a different size either as described above or by an embodiment having only one collimator opening which can be replaced by a collimator opening of another size. In both embodiment variants, an assortment of any number of collimator openings can be produced for any possible application. When the collimator openings are inserted into the cylindrical part, several cylindrical parts of different collimator opening sizes may be provided. All embodiments permit simple replacement of collimator openings in that a set of collimator openings of different sizes can be inserted into the collimator through replaceable sleeves of shielding material. The sleeves thereby advantageously have the same outer contour and contain only collimator openings of different sizes to permit variation of the collimator opening sizes simply through changing the sleeves.

The joining of shielding components always produces a slight gap even with high production accuracy, and it is therefore advantageous when the joined shielding components have no continuous contact surfaces extending parallel to the path of the rays. This may be provided by having them extend at angles other than that of the beams to be shielded. The contact surfaces of the components preferably have steps to prevent leakage radiation through gaps even when the scanning motion causes partial, parallel orientation of the joined parts with respect to the path of rays. This applies for all components located in the path of rays, such as the shielding block with cylindrical part as well as the replaceable sleeves with collimator openings.

In the embodiment comprising several collimator openings, the collimator openings which are not in the working position must be shielded as mentioned above. The shielding of these collimator openings is preferably provided by a further shielding block. The further shielding block may be disposed on the above-mentioned shielding block or be fixed to the collimator, wherein its extension is such that the collimator openings, which are not located in the working position, are disposed in the shadow of the further shielding block during each displacement of the collimator opening located in the working position—and therefore generally also of the shielding block. This embodiment is advantageous in that only the first-mentioned shielding block must be moved for scanning and not the further shielding block. This is important, since the shieldings consist of thick, heavy shielding metal. The reduced weight to be displaced makes the displacements and therefore the scanning process more flexible and simplifies extremely precise displacements.

The spherical surface-shaped path can be realized in various ways. The shielding block could have the shape of a cup and be movable on a spherical ring which does not cover the collimator opening located in the working position. The spherical surface-shaped path is preferably formed by two sliding rails which extend perpendicular to each other and on which the shielding block can be displaced. There are several possible designs. The sliding rails are preferably formed by rail pairs, wherein a first rail pair is rigidly connected to the collimator housing disposed on the radiation device, the second sliding pair has a first carriage which runs on the first rail pair, and the shielding block is disposed on a second carriage which runs on the second rail pair, which is preferably disposed perpendicular to the first rail pair. This produces stable bearing with defined motion such that each point on the spherical surface-shaped path can be reached, e.g. by a scanning motion in an x/y coordinate system associated with this spherical surface.

The drive means preferably has two drives for displacing the at least one collimator opening along the spherical surface-shaped path. Such drives in the x and y directions permit control to any position and can be easily controlled by a corresponding program such that irradiation can be carried out in accordance with a treatment plan. In the particular above-mentioned design, the drives are mounted on the carriages for moving same. The drives may be supported such that the drive of the first carriage is supported on the collimator housing and the second drive of the second carriage is supported on the first carriage. It is thereby essential that the drives have no play and can move large weights with little wear, since, as mentioned above, the shielding material is heavy. Towards this end, the drives may comprise e.g. ball screw spindles or roller screw spindles.

In a collimator having several collimator openings, the drive means advantageously comprises a further drive for moving the respective desired collimator opening into the working position. This may be effected in that the further drive is disposed on the shielding block to rotate the cylindrical part into the working positions of the collimator openings. In this manner, change of the collimator openings can be automated and all working steps can be carried out via computer control.

The drive means may be designed in various ways, but must permit electrical control by the control unit. They may be e.g. electromotive drives such as stepping motors, linear motors etc. It is also possible to use pneumatic or hydraulic drives with electric controls or hybrid drives or a combination of various drives.

The intensity of radiation can be controlled by designing the control unit such that the dwell time of the beams can be controlled by the drive means. The dwell time can preferably be obtained through the scanning speed of the beams at which these sweep over the object to be treated.

The control unit is preferably a computer running a corresponding program. This facilitates changes to the working mode by changing the software. To be able to verify all adjustments made, the collimator advantageously comprises position detecting means for the actuating motions. Since the control unit is preferably designed such that the scanning process is carried out in accordance with a predetermined treatment plan, the position detecting means offer verification and optional correction of the adjustments.

Universal computers are currently generally used for control and run a corresponding program for the exact control processes. For this reason, a program to control the inventive collimator is a further subject matter of the present invention. This program is suitably designed to control the drive means via a computer such that an object to be treated can be irradiated in correspondence with the predetermined contours, wherein, through actuation of the further drives, it selects the optimum collimator opening size for forming the contour and mutually matches the scanning processes, which are carried out with the different collimator openings, to obtain the required radiation.

To be able to subject the individual partial regions of the object to be treated to different radiation intensities, the program is advantageously designed such that the radiation intensity can be varied via the dwell time through corresponding control of the drive means.

A suitable working mode of the program may be subdivision of the respective treatment surface for an object to be treated into partial field segments and control of radiation via the computer in accordance with these partial field segments. Since an object to be treated is generally irradiated from different directions, the program performs subdivision of the radiation surfaces into partial field segments, in dependence on the different radiation directions.

The basis for irradiation is generally determined by previous detection of images of the object to be treated. For this reason, the program should be designed to determine the radiation surfaces on the basis of that detection of the contours by the imaging of the object to be treated. It may additionally determine the radiation surfaces for differing radiation intensities using detection of contours of those different partial regions of the object to be treated.

Since detected images are generally medically processed before radiation to establish a treatment plan, the program advantageously controls the drive means on the basis of images processed into a treatment plan. Determination of partial field segments is thereby also possible.

Of course, many modifications of the program are feasible. Only the substantial working steps which a computer must perform to control the collimator are mentioned herein.

BRIEF DESCRIPTION OF THE DRAWING

The invention is explained below with reference to the drawing.

DESCRIPTION OF THE PREFERRED EMBODIMENT

Figure 1:
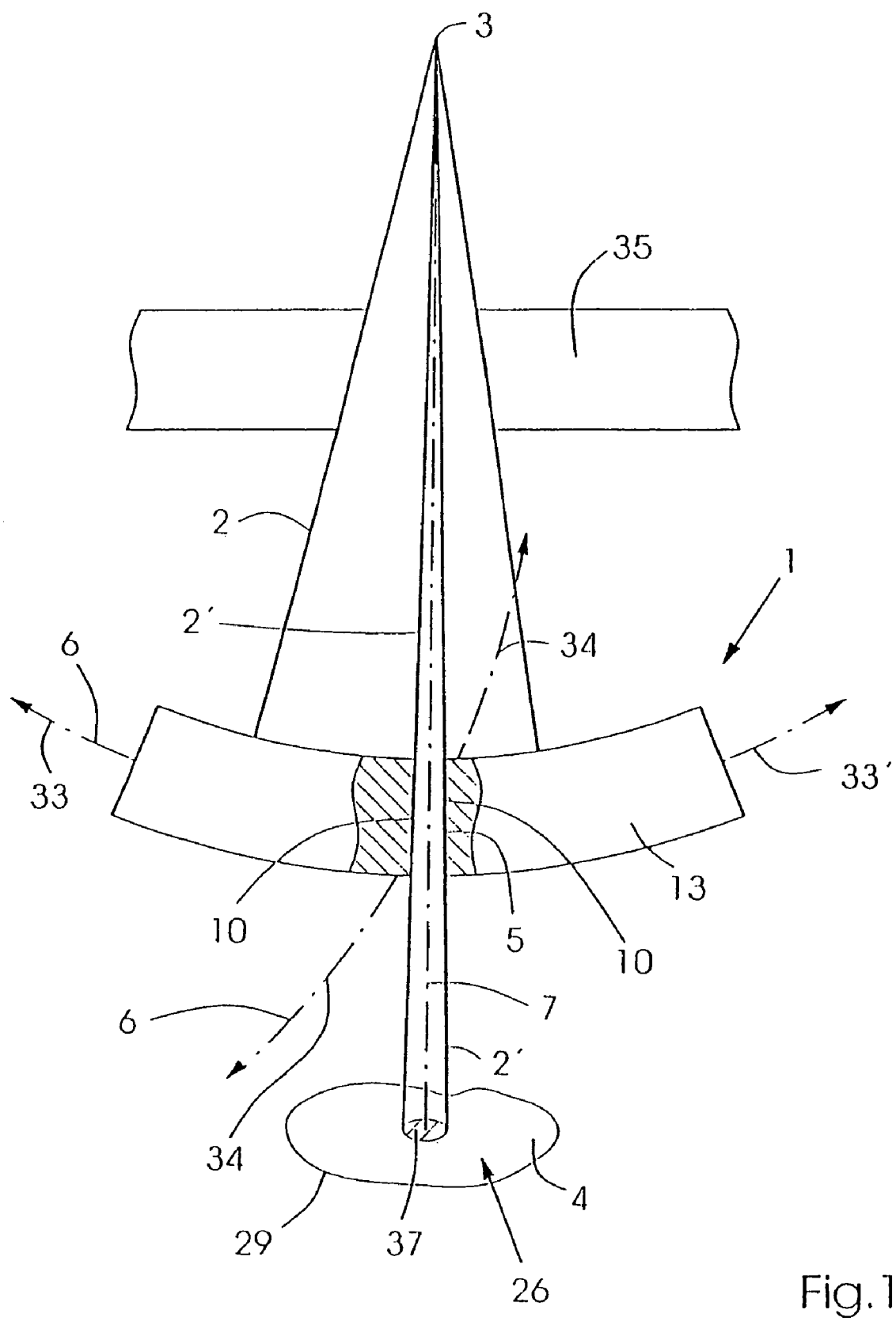
FIG. 1 shows a basic sketch of a collimator which was further developed in accordance with the invention and comprises some inventive features.

FIG. 1 shows a basic sketch of a collimator which was further developed in accordance with the invention in that a collimator opening 5 defines the beams 2 emitted by a radiation source 3 such that the beams are incident on a surface 37 which is substantially smaller than the surface 26 of the irradiation to be carried out. The collimator opening 5 is located in a shielding block 13 which can be displaced along a path 6 using a corresponding drive 8 (not shown herein) such that the beam 2' extending through the collimator opening 5 scans the surface 26 to be irradiated, thereby exposing same to the desired radiation. The radiation surface 26 thereby corresponds to the shape of the object to be treated 4 viewed in the radiation direction 27 of the currently performed radiation, as will be explained in more detail below.

Figure 2:
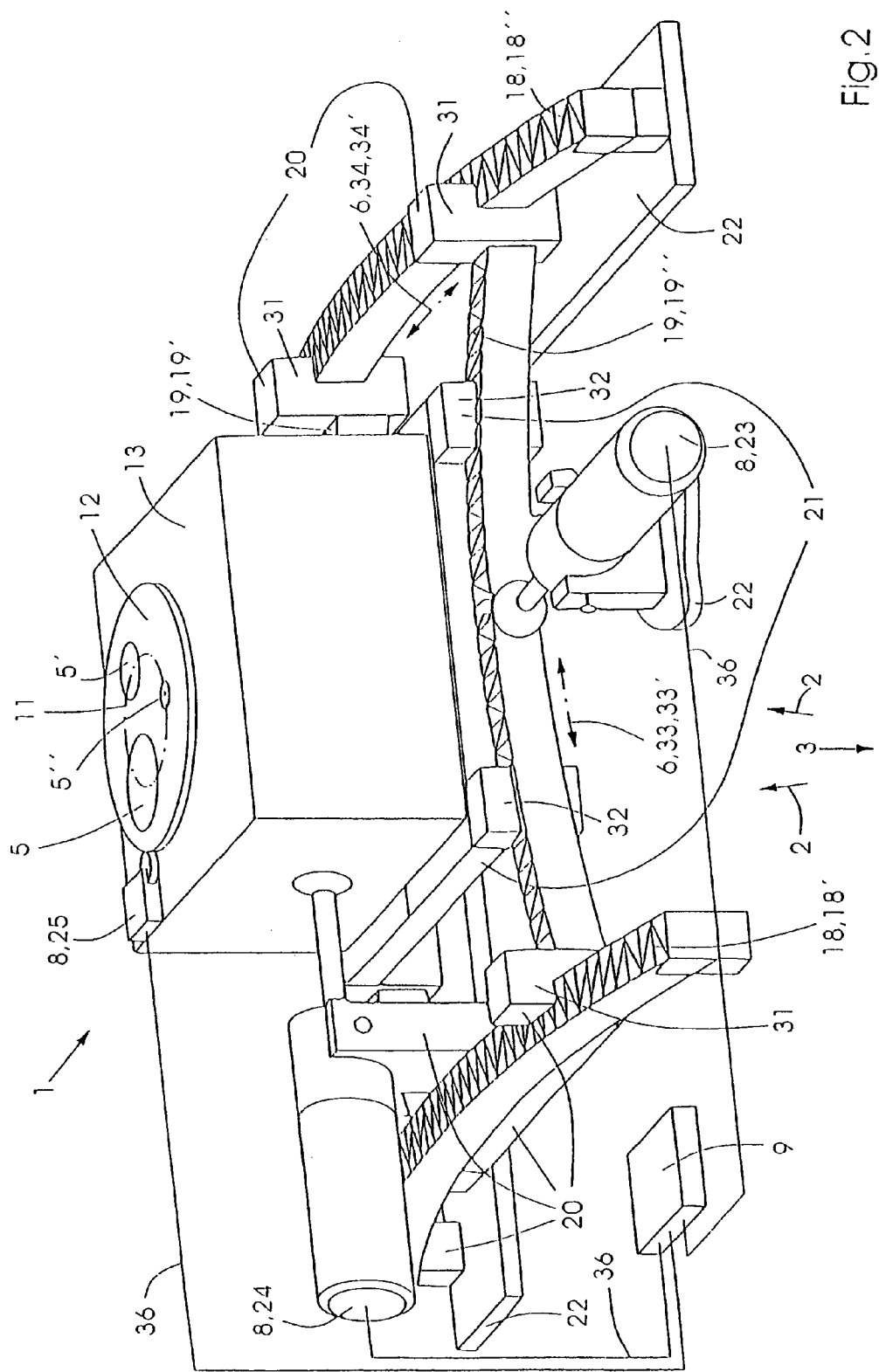
FIG. 2 shows a perspective view of an embodiment of the invention.

Some inventive embodiments are included in the drawing. The shielding block 13 with collimator opening 5 is displaced on a spherical surface-shaped path 6, wherein scanning motions 33, 33' in the x-direction, and scanning motions 34, 34' in the y-direction are performed relative to the spherical surface. The collimator opening 5 is thereby oriented such that its central axis 7 faces the radiation source 3. The limits 10 of the collimator opening 5 are moreover oriented to conically extend in the direction of the path of rays 2, 2' such that the full strength of the shielding block 13 is always provided for shielding, thereby preventing partial shadows caused by insufficient shielding. The shielding block 13 must thereby be guided while maintaining this collimator opening 5 orientation. One embodiment of such guidance is shown in FIG. 2. Other types of guidance are, of course, also possible.

FIG. 1 also shows that the beams 2' emitted by the radiation source 3 are conventionally defined by a pre-collimator 35, wherein the opening of this pre-collimator 35 is dimensioned such that it shields all regions located outside of the shielding of the shielding block 13 such that the shielding block 13 shields the beams 2 passing through the pre-collimator in any possible position, except for the beams 2' passing through its collimator opening 5. The opening of the pre-collimator could of course also be variable or displaceable.

FIG. 2 shows a perspective view of an embodiment of the invention. The radiation source 3 is located below the collimator 1 and the beams 2 impinge on the collimator 1 from this direction. The radiation source 3 and pre-collimator 35 are not shown for reasons of clarity.

This embodiment shows realization of a drive 8. To permit motion along the spherical, surface-shaped path 6, a first sliding rail 18 is initially disposed in a collimator housing 22 (only partially shown). This first sliding rail 18 consists of a rail pair 18' and 18" which have arcuate shapes such that the centers of these two arcs are disposed on an axis which passes through the substantially punctiform radiation source 3. A first displaceable carriage 20 is disposed on this first sliding rail 18 which has bearings 31 which run on the first sliding rail 18. A second rail pair 19' and 19" form a second sliding rail 19 which extends perpendicular to the fist sliding rail 18. The rail pair 19' and 19" of the second sliding rail 19 are also arc-shaped, with the centers of these arcs also being disposed on an axis which extends through the radiation source 3. A second carriage 21 is disposed on the second sliding rail 19 and can be displaced via bearings 32. The shielding block 13 which carries the collimator openings 5, 5', 5" is located on this second carriage 21.

The two carriages 20 and 21 permit displacement along the spherical surface-shaped path 6. Scanning motions 33, 33' in the x-direction and 34, 34' in the y-direction are thereby possible. A drive 23 for the first carriage 20 is disposed on the collimator housing 22. This drive performs the scanning motions 34, 34'. A drive 24 for the second carriage 21 is disposed on the first carriage 20 and provides displacement in the x-direction, i.e. executes scanning motions 33 and 33'. Also in this case, the x- and y-directions do not refer to a straight surface but to the spherical surface of the spherical surface shaped path 6.

To provide scanning motions 33, 33', 34, 34' such that a radiation surface 26 can be exposed to the predetermined radiation, a control unit 9 is provided which is connected to the drives 23 and 24 via the connections 36. One embodiment for carrying out such a scanning motion through the control 9 is explained below.

The embodiment of the collimator 1 shown is moreover provided with a means for automatic change of the collimator openings 5, 5', 5". Towards this end, a cylindrical part 12 is disposed in the shielding block 13, which can be rotated and be brought into predetermined positions via a further drive 25. This further drive 25 is also connected via a connection 36 to the control unit 9 which provides the actuation commands for changing the collimator openings 5, 5', 5". The collimator openings 5, 5', 5" are arranged such that one of these collimator openings 5, 5' or 5" is always in the working position in which its central axis 7 is oriented towards the radiation source 3, as already explained in FIG. 1. The arrangement of the collimator openings 5, 5', 5" is advantageously selected such that they move on an imaginary circular path 11 which is dimensioned such that the collimator openings 5, 5', 5" can be moved into the working position through rotation of the cylindrical part 12.

This embodiment requires, of course, that the collimator openings 5, 5'; 5', 5" or 5, 5" which are not in the working position, are located in a shielded region. This could be provided through corresponding design of the pre-collimator 35 or in the manner shown in FIG. 3.

Figure 3:
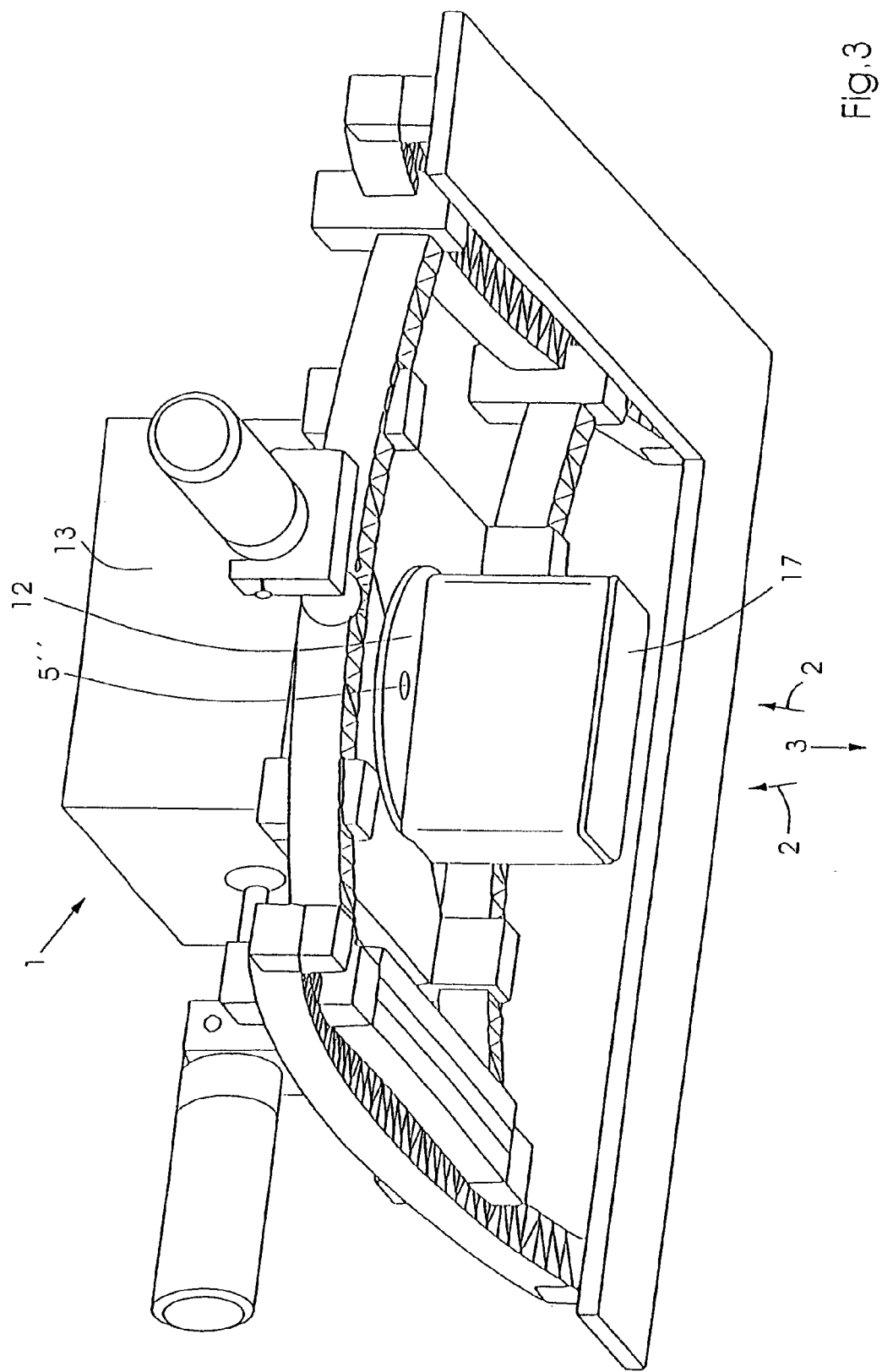
FIG. 3 shows the same embodiment from a different perspective with a further shielding block.

FIG. 3 shows the same embodiment as FIG. 1 from a different perspective showing the further shielding block 17 which shields the collimator openings 5 and 5' which are not in the working position. Only the collimator opening 5" which is in the working position, is not shielded. This further shielding block 17 may be provided on a second carriage 21 e.g. on the first shielding block 13. To reduce the weight to be moved, the further shielding block 17 could also be mounted to the collimator housing 22 which requires that its size and the actuating motions of the scanning motion are mutually matched to ensure that the collimator openings 5 and 5' which are not in the working position, are always located in the shielded region of the further shielding block 17. The latter could, of course, also be displaceable.

Figure 4:
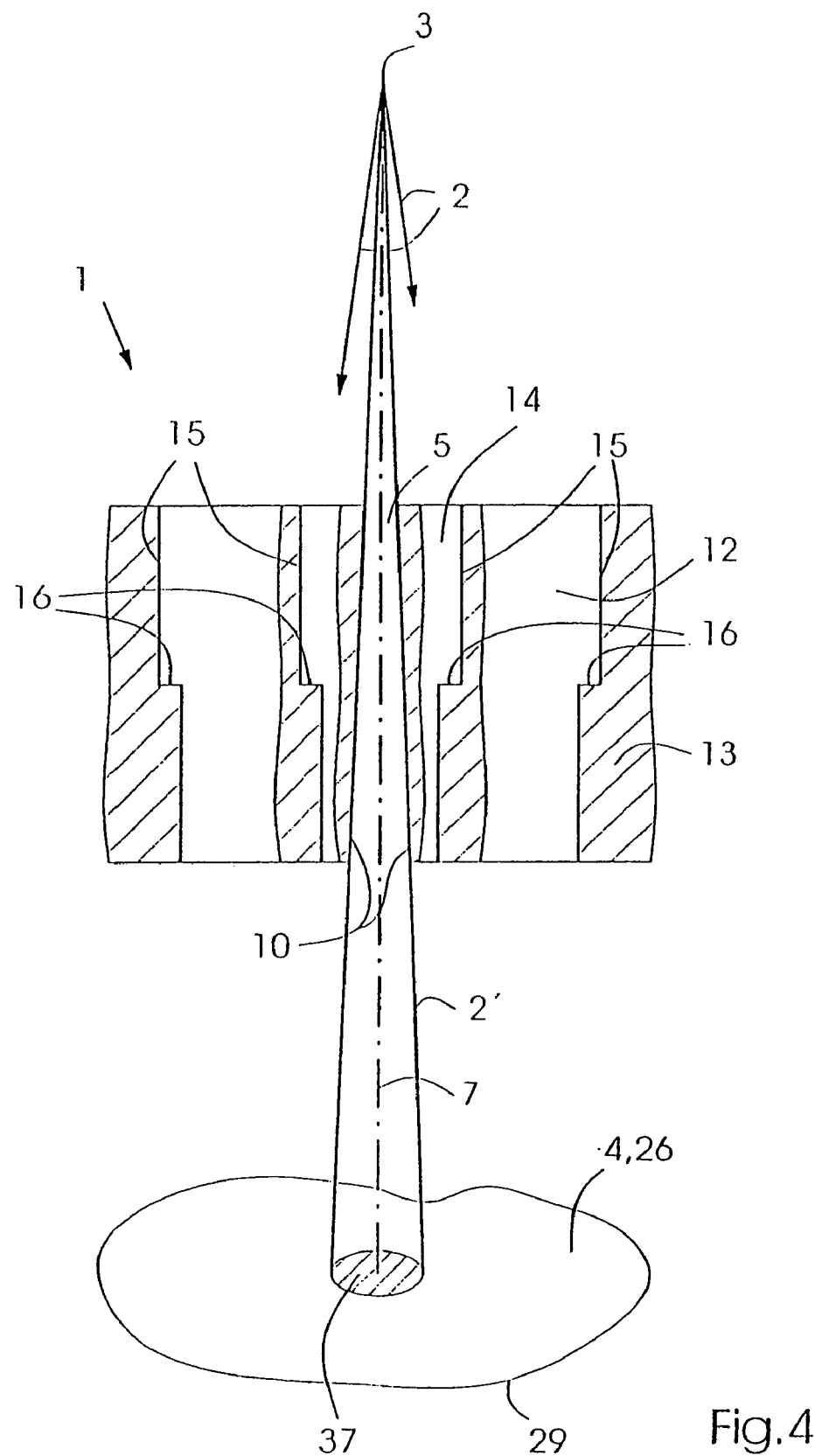
FIG. 4 shows a section of an embodiment of the inventive collimator.

FIG. 4 shows a section of a design of an inventive collimator 1. This collimator could be the one from FIGS. 2 and 3 or an inventive collimator 1 of different design. In any case, this collimator 1 consists of a shielding block 13 containing a cylindrical part 12 disposed to be rotatable and having collimator openings 5, 5' and 5". The illustration shows a partial section through the shielding block 13 thereby illustrating the design and insertion of the cylindrical part 12 and that the collimator opening 5 is disposed on a sleeve 14 which is disposed in the cylindrical part 12. The other collimator openings 5' and 5" are suitably inserted into the cylindrical part 12 via sleeves 14 (not shown). This design permits insertion of collimator openings 5, 5', 5" of any size into the collimator 1 due to the replaceability of these collimator openings 5, 5', 5" in dependence on the requirements for irradiation, whether large collimator openings 5 for large surfaces 26 or medium 5' or small collimator openings 5" for exact finishing of the contours 29 of the fields 26 to be irradiated are required.

The drawing also shows that the contact surfaces 15 advantageously have steps 16 to prevent leaking radiation from penetrating through them when they extend in a region in the direction of the path of rays 2 at a given position of the shielding block 13.

One embodiment is, of course, feasible, with which the cylindrical parts 12 are exchanged to provide more than the collimator openings 5, 5', 5" of various sizes located on the part 12. The solution with the sleeves 14 is advantageous in that it is less expensive (in view of the expensive shielding material) and also since the drive 25 (which was omitted in FIG. 4) for changing the sleeves 14 need not be disengaged which would be the case for changing the cylindrical parts 12.

Figure 5:
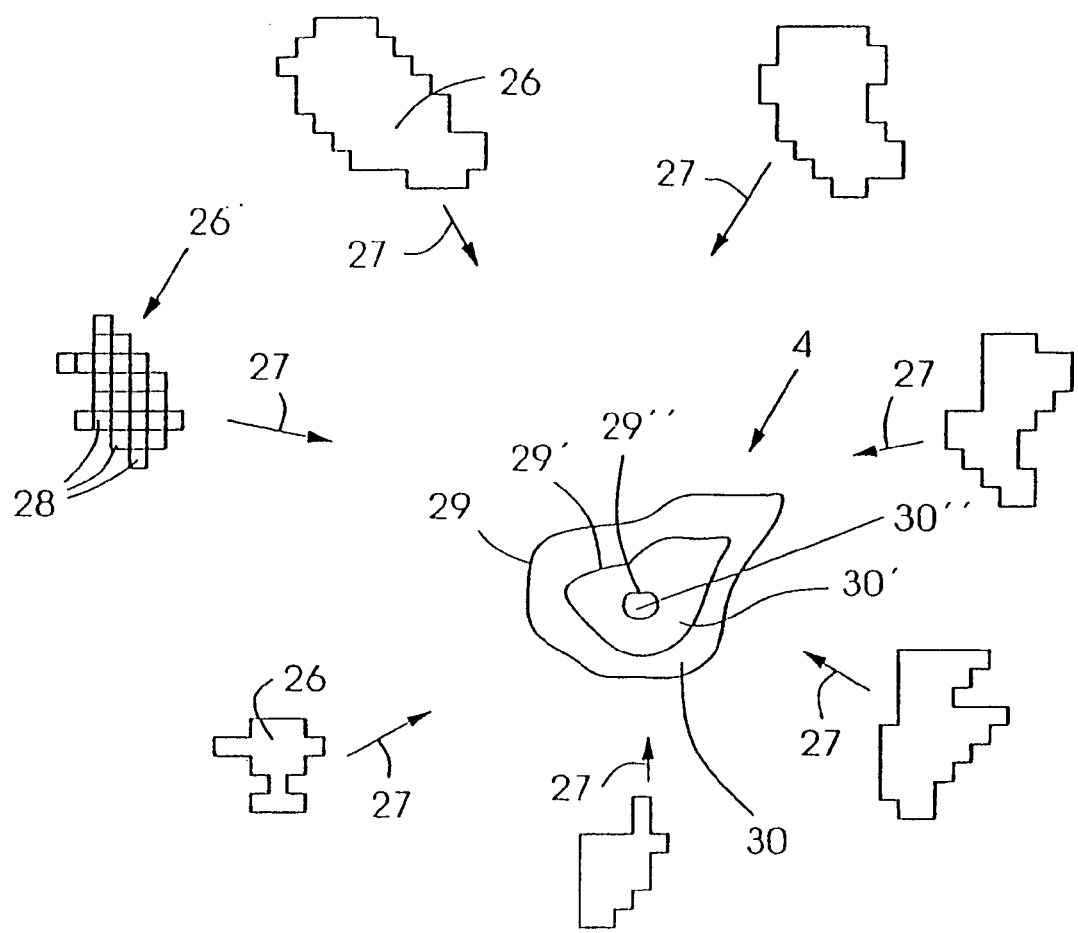
FIG. 5 shows the principle of a radiation concept realized through a program.

FIG. 5 illustrates an irradiation plan realized by a program. The objects to be treated 4 are usually irradiated from different treatment directions 27 to obtain high irradiation of the object to be treated 4 with relatively little irradiation of the surrounding tissue. Since the objects to be treated 4 have an irregular shape, one radiation surface 26 must be selected for each radiation direction 27 which corresponds to the shape of the object to be treated 4—viewed from the respective radiation direction 27. The shape of the object to be treated 4 is advantageously detected through imaging to determine at least the radiation surfaces 26 from the different radiation directions 27. To be able to irradiate these surfaces 26, a program associates these radiation surfaces 26 with partial field segments 28 to apply the corresponding beams 2' to these partial field segments 28 during irradiation. The application of squarely collimated radiation is shown as an example to better illustrate the principle. Round collimator openings 5, 5', 5" are preferred to avoid steps.

The object to be treated, 4 in the figure, has a contour 29 which does not correspond to the illustrated radiation directions 27 but to the direction of the viewer. The object to be treated 4 should indeed be envisioned as three-dimensional. Contours 29, 29', 29" of corresponding different shape of the object to be treated 4 and of regions thereof which must be irradiated with higher intensities 30', 30" for each radiation direction 27. The contours 29, 29', 29" show the principle which is based on the fact that the object to be irradiated 4 should not be irradiated with the same intensity and uniform distribution, rather different intensities 30, 30', 30" are provided which are each delimited by contours 29, 29', 29". Towards this end, a further design of the radiation concept is advantageous which is explained with reference to FIGS. 6 and 6a.

Figure 6:
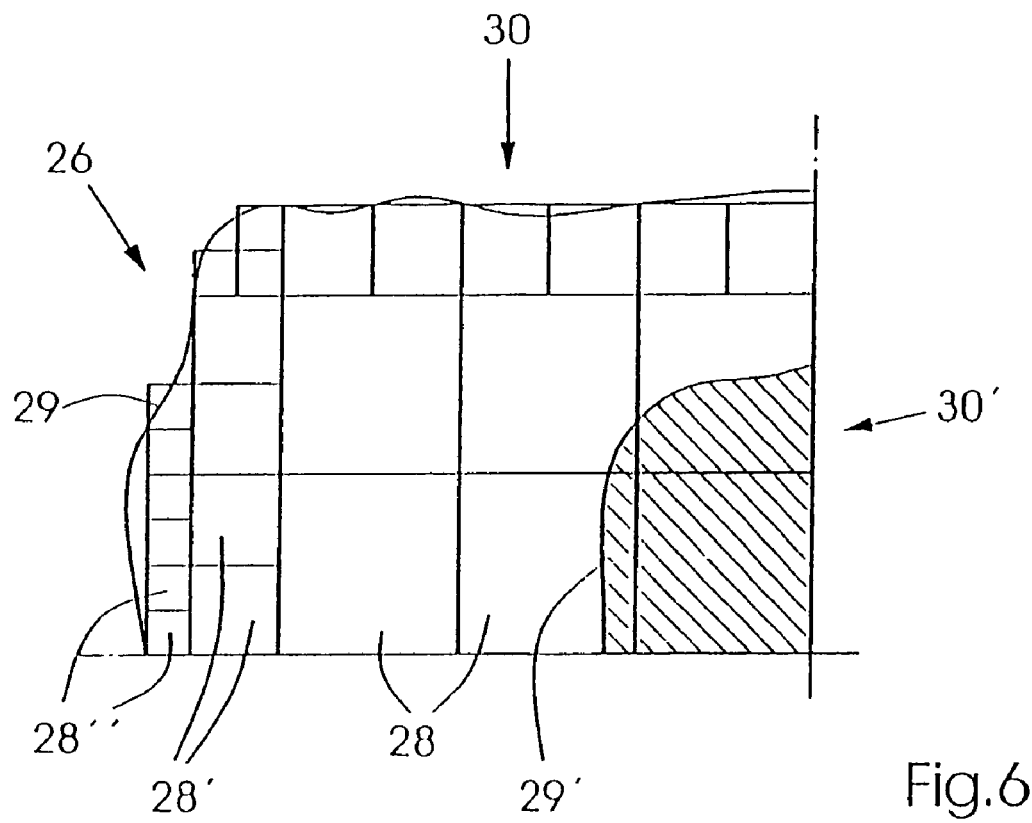
FIG. 6 shows a further design of the radiation concept with reference to the embodiment provided by the invention.

FIG. 6 shows such a design of the radiation concept, wherein two radiation intensities 30 and 30' are shown as an example. The drawing does not show the entire radiation surface 26 but merely a section which is delimited by the dash-dotted lines. Shown are the two contours 29 and 29' for the desired radiation intensities 30, 30'. The different radiation intensities 30 and 30' may be obtained by first irradiating the surface 26 shown in FIG. 6 with a certain radiation intensity 30 and subsequently repeating irradiation within the contour 29' to obtain intensity 30'. Clearly, it would also be possible to initially subject the region between the contours 29 and 29' to a first intensity 30 and subsequently irradiate the region delimited by the contour 29' with a second intensity 30'.

Figure 6A:
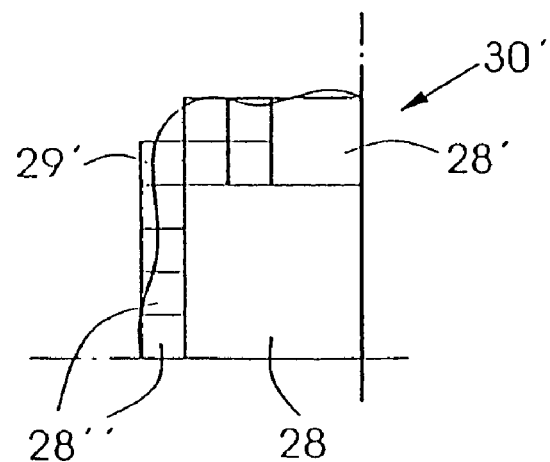
FIG. 6a shows a section from FIG. 6.

In contrast to FIG. 5, FIGS. 6 and 6a show a further possibility of radiation providing collimator openings 5, 5', 5" of different sizes in accordance with the invention. In this manner, the radiation surfaces 26 can be subdivided into partial field segments 28, 28', 28" of different sizes to realize different contours 29 and different contours 29, 29', 29" with radiation intensities 30, 30', 30" of different strengths. The drawing is simplified and shows two radiation intensities 30 and 30', wherein FIG. 6 shows a first radiation of large partial field segments 28 and, depending on the travel of the contour 29, of medium partial field segments 28' and small partial field segments 28". In accordance with FIG. 6a, the region to be irradiated with higher intensity 30' is once more irradiated. Also in this case, the contour 29' is filled by the partial field segments 28, 28', 28". The extent to which the contour itself or surrounding tissue should also be irradiated or whether parts within the contour 29 or 29'should not be irradiated must be decided by the physician. Instead of two irradiations, the scanning speed may be varied to obtain various radiation intensities 30, 30', 30". The field may thereby be coarsely scanned with large collimator openings 5, 5' and subsequently with small collimator openings 5', 5", with precise limitations.

Of course, other embodiments of the invention are also feasible. The shielding block 13 could e.g. have the shape of a spherical shell, i.e. similar to FIG. 1, wherein such a spherical shell is disposed on a ring which is complementary to this shape. Displacement on a spherical surface-shaped path 6 would also be possible in this case. It would also be feasible to provide such a shielding block 13 with only one collimator opening which may be disposed in a sleeve 14 to change the size of the collimator opening 5, 5', 5", ... by changing the sleeves 14. It would also be possible to dispose the collimator opening 5, 5', 5" and optionally further collimator openings in a different manner, to move the currently desired collimator opening into the working position and to shield the others.

Of course, in view of the design of the radiation concept, other methods are also feasible, e.g. to directly follow the contours 29, 29' or 29" through surfaces 37 of radiation loading in an analogous manner and then filling the rest of the surfaces 26, optionally with larger collimator openings. In particular, round collimator openings 5, 5', 5" are thereby suitable. The filling may also be effected by always following, in accordance with the contour 29, 29', 29", the inner edge of the already irradiated surface until the surface 26 has been completely filled. Further embodiments of the collimator 1 and of the irradiation concept on which the control 9 or the program are based, are feasible.

LIST OF REFERENCE NUMERALS

1 Collimator
2,2' Beams/path of rays
2' Beams defined by the collimator 1
3 Radiation source
4 Object to be treated
5,5',5" Collimator openings
5 Large
5' Medium
5" Small
6 (spherical surface-shaped) path
7 central axis of the collimator opening
8 drive means
9 control unit
10 limits of the collimator opening
11 imaginary circular path
12 cylindrical part
13 shielding block
14 sleeves
15 contact surfaces
16 steps
17 further shielding block
18 first sliding rail
18', 18" first rail pair
19 second sliding rail
19', 19" second rail pair
20 first carriage
21 second carriage
22 collimator housing (partially shown)
23 first carriage drive
24 second carriage drive
25 Further drive
26 Radiation surface/surface to be radiated
27 Radiation directions
28,28',28" Partial field segments
29,29',29" Contour
29', 29" Contour of a radiation surface of higher intensity
30,30',30" Radiation intensities
30',30" Higher intensities
31 First carriage bearings
32 Second carriage bearings
33,33' Scanning motion in the x-direction
34,34' Scanning motion in the y-direction
35 Pre-collimator
36 Connection of control to the drives
37 Area irradiated by the beam defined by the collimator

We claim:

1. A collimator for defining a beam of high energy rays which is emitted from a substantially punctiform radiation source and directed onto an object to be treated and adaptable to stereotactic conformation irradiation of tumors, the collimator being designed to scan an irregular object to be treated using the beam defined by a collimator opening, the collimator comprising:

means defining a plurality of collimator openings having differing sizes;

means for positioning said defining means to select one of said plurality of openings and for displacing said selected opening in any desired direction along a spherical surface shaped path, wherein a control axis of said selected opening remains oriented towards the radiation source, with non-selected collimator openings being shielded from radiation;

a drive means cooperating with said positioning means for selecting said selected opening and for displacing said selected opening; and a control communicating with said drive means to command positioning of said defining means and displacement of said selected collimator opening, wherein large collimator openings are used for scanning large portions of a radiation surface of the object to be treated and small collimator openings are used for exact definition at edges of said radiation surface and for treatment of radiation surfaces having irregular contours.

2. The collimator of claim 1, wherein at least one collimator opening has delimitations extending in a direction of a path of the rays.

3. The collimator of claim 1, wherein at at least one collimator opening is round.

4. The collimator of claim 1, wherein at at least one collimator opening is four sided.

5. The collimator of claim 1, wherein said defining means are disposed to rotate said plurality of collimator openings along an imaginary circular path.

6. The collimator of claim 5, wherein said defining means comprise a cylindrical part of shielding material which can be rotated through a revolver-like mechanism and be fixed in individual working positions of respective selected openings.

7. The collimator of claim 6, further comprising a first shielding block in which said cylindrical part is rotatably disposed.

8. The collimator of claim 1, further comprising means for replacing at least one collimator opening with at least one collimator opening having a different size.

9. The collimator of claim 8, wherein said replacing means have a set of collimator openings of different sizes which are inserted into said defining means using replaceable sleeves of shielding material.

10. The collimator of claim 6, wherein adjacent shielding components have no continuous contact surfaces which extend parallel to a path of the rays.

11. The collimator of claim 6, wherein contact surfaces of components have steps.

12. The collimator of claim 1, further comprising a second shielding block to shield collimator openings which are not in a working position.

13. The collimator of claim 12, further comprising a first shielding block on which said additional shielding block is disposed.

14. The collimator of claim 13, wherein said second shielding block is fixed to said first shielding block and is structured and dimensioned such that collimator openings which are not in a working position are located in a shadow of said second shielding block for each displacement of said selected collimator opening.

15. The collimator of claim 1, wherein said positioning means comprises by two mutually perpendicular sliding rails on which said defining means is displaceably disposed.

16. The collimator of claim 15, wherein said sliding rails are formed by rail pairs, wherein a first rail pair is fixed with respect to the radiation source and a second rail pair cooperates with a first carriage which runs on said first rail pair, said defining means being disposed on a second carriage which runs on said second rail pair.

17. The collimator of claim 1, wherein said drive means comprise a first and a second drive to displace said selected collimator opening along said spherical surface-shaped path.

18. The collimator of claim 16, wherein said first drive is disposed on said first carriage and said second drive is disposed on said second carriage.

19. The collimator of claim 17, wherein said drive means comprise ball screw spindles.

20. The collimator of claim 17, wherein said drive means comprise roller screw spindles.

21. The collimator of claim 1, wherein said drive means comprise a third drive to move said selected collimator opening into a working position.

22. The collimator of claim 21, wherein said third drive is disposed on a shielding block to rotate said defining means into working positions of said collimator openings.

23. The collimator of claim 1, wherein said drive means has at least one electromotive drive.

24. The collimator of claim 1, wherein said drive means comprises at least one pneumatic drive.

25. The collimator of claim 1, wherein said drive means comprises at least one hydraulic drive.

26. The collimator of claim 1, wherein said control is designed to control a dwell time of the beams via said drive means.

27. The collimator of claim 26, wherein said control is designed such that said dwell time is defined by a scanning speed of beams sweeping over the object being treated.

28. The collimator of claim 1, wherein said control comprises a computer having a corresponding program.

29. The collimator of claim 1, further comprising position detecting means for actuating motions.

30. The collimator of claim 1, wherein said control is arranged such that a scanning process is carried out in accordance with a predetermined treatment plan.

31. The collimator of claim 29, wherein said control is connected to said position detecting means such that said position detection means verifies and corrects said actuating motions.

32. A method for controlling the collimator of claim 1, the method comprising the steps of:
a) controlling said drive means via a programmed computer such that the object to be treated is irradiated in accordance with a predetermined contour; and
b) selecting an optimum size of a collimator opening for irradiating said contour through actuation of said drive means to mutually match scanning processes which are carried out with different collimator openings for obtaining a required radiation exposure.

33. The method of claim 32, further comprising the step of varying a radiation intensity via a dwell time by means of appropriable control of said drive means.

34. The method of claim 32, further comprising subdividing a respective radiation surface for an object to be treated into partial field segments and controlling radiation via said computer in accordance with these partial field segments.

35. The method of claim 34, wherein said subdividing into partial field segments of said radiation surface is effected in dependence on different radiation directions from which the object to be treated is irradiated.

36. The method of claim 1, wherein radiation surfaces are determined on a basis of detection of contours through imaging of the object to be treated.

37. The method of claim 36, wherein radiation surfaces with different radiation intensities are determined on a basis of detection of contours of different partial regions of the object to be treated.

38. The method of claim 32, wherein said drive means are controlled on a basis of imaging processing through a treatment plan.

* * * * *